(12) United States Patent
Matsuno

(10) Patent No.: US 6,556,912 B2
(45) Date of Patent: Apr. 29, 2003

(54) ROAD FRICTION COEFFICIENT ESTIMATING APPARATUS

(75) Inventor: Koji Matsuno, Tokyo (JP)

(73) Assignee: Fuji Jukogyo, Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/883,783

(22) Filed: Jun. 18, 2001

(65) Prior Publication Data

US 2002/0002437 A1 Jan. 3, 2002

(30) Foreign Application Priority Data

Jun. 29, 2000 (JP) ........................................ 2000-197203

(51) Int. Cl.$^7$ ................................................ B62D 6/00
(52) U.S. Cl. ............................ 701/80; 701/74; 701/73; 73/9; 303/139; 303/146; 303/150
(58) Field of Search ............................. 701/80, 73, 74; 303/139, 140, 146, 147, 148, 149, 150; 73/9

(56) References Cited

U.S. PATENT DOCUMENTS

| | | | | |
|---|---|---|---|---|
| 5,198,982 A | * | 3/1993 | Kobayashi | 180/197 |
| 5,394,329 A | * | 2/1995 | Bridgens | 180/197 |
| 5,493,893 A | * | 2/1996 | Kin et al. | 701/82 |
| 5,719,565 A | * | 2/1998 | Tsuno et al. | 340/442 |
| 6,015,192 A | * | 1/2000 | Fukumura | 303/140 |

FOREIGN PATENT DOCUMENTS

| | | |
|---|---|---|
| JP | 7-186989 | 7/1995 |
| JP | 8-002274 | 1/1996 |

* cited by examiner

Primary Examiner—Michael J. Zanelli
Assistant Examiner—Eric M Gibson
(74) Attorney, Agent, or Firm—Frishauf, Holtz, Goodman & Chick, P.C.

(57) ABSTRACT

A control section of a road friction coefficient estimating apparatus inputs a vehicle speed, a steering wheel angle and a yaw rate from a vehicle speed sensor, a steering wheel angle sensor and a yaw rate sensor, respectively. The control section comprises a reference yaw rate calculating section, a yaw rate deviation calculating section, a yaw rate deviation dispersion calculating section and a road friction coefficient establishing section. The reference yaw rate calculating section calculates a reference yaw rate based on vehicle speed and steering angle in accordance with a vehicle motion model. The yaw rate deviation calculating section calculates a yaw rate deviation based on the reference yaw rate and the actual yaw rate. The yaw rate deviation dispersion calculating section calculates a dispersion of the yaw rate deviation for a specified sampling number. The road friction coefficient establishing section establishes and outputs a road friction coefficient by referring to a look-up table parameterizing the dispersion.

14 Claims, 7 Drawing Sheets

ROAD FRICTION COEFFICIENT ESTIMATING APPARATUS

BACKGROUND OF THE INVENTION

1. Field of the Invention

The present invention relates to an apparatus for estimating friction coefficients on road surfaces and particularly to an apparatus for estimating friction coefficients more accurately.

2. Discussion of Related Arts

In recent years, numerous vehicle control technologies such as a traction control technology, a braking force control technology, a torque distribution control technology and the like, have been proposed and some of these control technologies have been realized in actual automobile markets. Many of these control technologies use a friction coefficient on a road surface (hereinafter, referred to as road friction coefficient) for calculation or correction of control parameters. Accordingly, in order to make the control sure and precise, it is necessary to estimate accurate road friction coefficients.

There are several technologies in which road friction coefficients are estimated. For example, Japanese Patent Application Laid-open No. Toku-Kai-Hei 7-186989 discloses a technology in which a road friction coefficient is calculated according to a deviation of lateral acceleration. The deviation of lateral acceleration is a difference between an estimated lateral acceleration based on an actual yaw rate detected by a yaw rate sensor and an actual lateral acceleration detected by a lateral acceleration sensor.

Further, in Japanese Patent Application Laid-open No. Toku-Kai-Hei 8-2274 an inventor of the present invention proposes a technology wherein road friction coefficients are estimated based on the theory of adaptive control according to an equation of motion about a lateral motion of a vehicle using steering wheel angle, vehicle speed, yaw rate and other parameters.

However, Toku-Kai-Hei 7-186989 has a problem that the accuracy of estimation of road friction coefficient is easily influenced by resolution or noises of sensors. Accordingly, many conditions such as effective zero corrections, shield, a proper fitting position and the like are required from the sensors. Further, Toku-Kai-Hei 8-2274 has a disadvantage that since the principle of estimating road friction coefficients is based on a change of dynamic characteristics of vehicle motion according to the difference of road friction coefficients, it is difficult to detect road friction coefficients without vibratory steering inputs.

SUMMARY OF THE INVENTION

It is an object of the present invention to provide a road friction coefficient estimating apparatus which is capable of minimizing the influences of resolution, zero correction and noises of sensors, and which can estimate accurate road friction coefficients without vibratory steering inputs.

To accomplish the object, a road friction coefficient estimating apparatus for a vehicle according to a first aspect of the present invention comprises a reference value calculating means for calculating a reference value of the parameter, an actual value detecting means for detecting an actual value of a parameter indicative of a condition of motion of the vehicle, a deviation calculating means for calculating a deviation of the actual value from the reference value, a dispersion calculating means for calculating a dispersion obtained by statistically processing the deviation with a specified sampling number, and a road friction coefficient establishing means for establishing a road friction coefficient based on the dispersion. It is preferable to assign a yaw rate or a lateral acceleration to the parameter.

A road friction coefficient estimating apparatus for a vehicle according to a second aspect of the present invention comprises a momentary steering characteristic calculating means for calculating a steering characteristic at each moment based on an actual condition of motion of the vehicle, a dispersion calculating means for calculating a dispersion obtained by statistically processing the steering characteristic with a specified sampling number, and a road friction coefficient establishing means for establishing a road friction coefficient based on the dispersion.

DETAILED DESCRIPTION OF PREFERRED EMBODIMENTS

Figure 1:
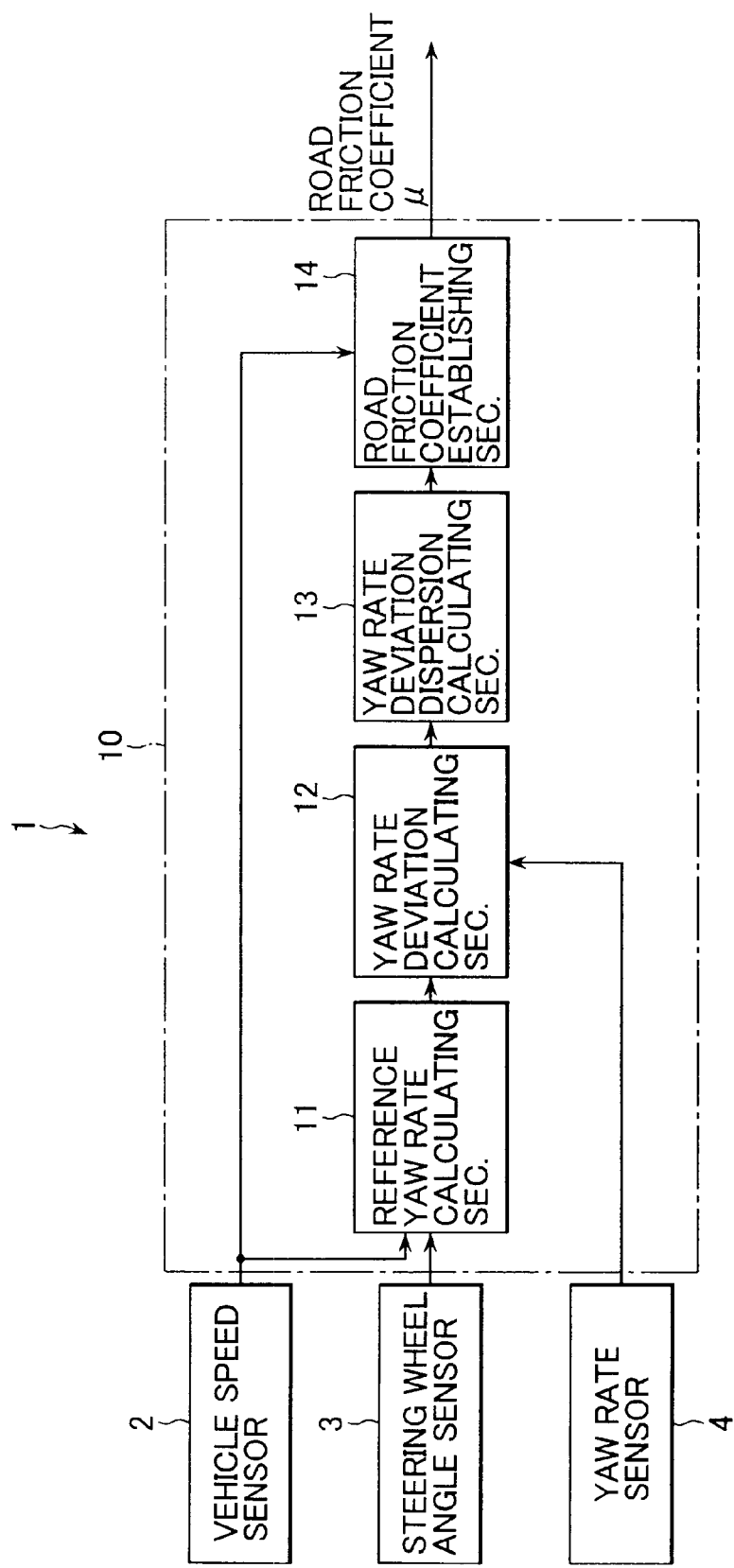
FIG. 1 is a functional block diagram showing a road friction coefficient estimating apparatus according to a first embodiment of the present invention.

Referring now to FIG. 1, reference numeral 1 denotes a road friction coefficient estimating apparatus for estimating road friction coefficients, whose control section 10 is connected with a vehicle speed sensor 2, a steering wheel angle sensor 3 and a yaw rate sensor 4 for inputting a vehicle speed V indicative signal, a steering wheel angle $\theta H$ indicative signal and a yaw rate (yaw angular velocity) $\gamma$ indicative signal, respectively.

The control section 10 of the road friction coefficient estimating apparatus 1 is constituted by a micro-computer and peripheral circuits and functionally constituted by a reference yaw rate calculating section 11, a yaw rate deviation calculating section 12, a yaw rate deviation dispersion calculating section 13 and a road friction coefficient establishing section 14.

The reference yaw rate calculating section 11 inputs a vehicle speed V indicative signal from the vehicle speed sensor 2, a steering wheel angle $\theta H$ indicative signal from the steering wheel angle sensor 3 and calculates a reference value $\gamma 0$ of yaw rate $\gamma$ according to the following formula (1) based on a vehicle motion model:

$$\gamma 0 = (G\gamma\delta(\theta H/n))/(1+tr\cdot s) \qquad (1)$$

where n is a steering gear ratio; $G\gamma\delta$ is a yaw rate gain; tr is a time constant of first order lag and s is a Laplace operator.

Further, the yaw rate gain $G\gamma\delta$ is also expressed as the following formula (2):

$$G\gamma\delta=(1/(1+A\cdot V^2))\cdot(V/L) \quad (2)$$

Where A is a stability factor which is expressed as follows:

$$A=-(M/(2\cdot L^2))\cdot(L_f K_f - L_r K_r)/(K_f K_r) \quad (3)$$

where M is a mass of vehicle; $L_f$ is a distance between a center of gravity of a vehicle and a front axle; $L_r$ is a distance between a center of gravity of a vehicle and a rear axle; $K_f$ is an equivalent cornering power of a front wheel and $K_r$ is an equivalent cornering power of a rear wheel.

Further, the first order lag time constant tr is expressed as:

$$tr=(Iz\cdot V)/(2\cdot(K_f+K_r)\cdot L_f L_r) \quad (4)$$

where Iz is a yaw inertia moment.

Thus, according to the formula (1), the reference yaw rate $\gamma 0$ is obtained in consideration of dynamic lag. Accordingly, even when a driver makes a fast steering, an accurate value of the reference yaw rate $\gamma 0$ can be obtained.

The yaw rate deviation calculating section 12 inputs an actual yaw rate $\gamma$ from the yaw rate sensor 4 and inputs a reference yaw rate $\gamma 0$ from the reference yaw rate calculating section 11. The yaw rate deviation calculating section 12 calculates a deviation (yaw rate deviation) $\Delta\gamma$ of the actual yaw rate $\gamma$ from the reference yaw rate $\gamma 0$ and outputs the deviation to the yaw rate deviation dispersion calculating section 13.
That is:

$$\Delta\gamma=\gamma-\gamma 0 \quad (5)$$

The yaw rate deviation dispersion calculating section 13 inputs a yaw rate deviation $\Delta\gamma$ from the yaw rate deviation calculating section 12 and calculates a dispersion $V\gamma$ of the yaw rate deviation $\Delta\gamma$ in a predetermined sampling number according to the following formula (6). The calculated dispersion $V\gamma$ is outputted to the road friction coefficient establishing section 14.

$$V\gamma=(1/m)\Sigma(\Delta\gamma i - \Delta\gamma c)^2 \quad (6)$$

where m is a sampling number; i is a data number of the yaw rate deviation $\Delta\gamma$; $\Delta\gamma c$ is an average of the total yaw rate deviations $\Delta\gamma$ for the sampling number m; and $\Sigma$ is a sum from 1 to m.

Figure 2:
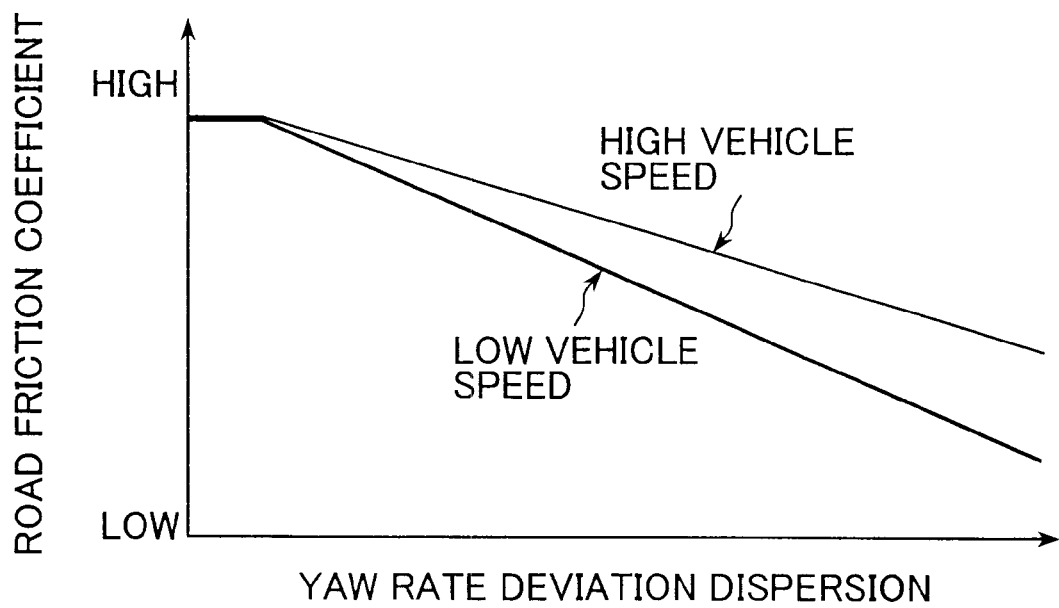
FIG. 2 is a schematic diagram showing a look-up table indicative of road friction coefficient versus yaw rate deviation dispersion.

The road friction coefficient establishing section 14 inputs the vehicle speed V from the vehicle speed sensor 2 and the yaw rate deviation dispersion $V\gamma$ from the yaw rate deviation dispersion calculating section 13, respectively and establishes a road friction coefficient $\mu$ based on these values. Specifically, the road friction coefficient is established by referring to a look-up table as shown in FIG. 2. The look-up table is prepared experimentally beforehand based on the relationship between road friction coefficient $\mu$ and yaw rate deviation dispersion.

As understood from the table, since the grip force of tire becomes lower as road friction coefficients becomes low, the yaw rate deviation dispersion $V\gamma$ becomes large. Further, as vehicle speeds go up, the yaw rate deviation dispersion $V\gamma$ tends to become larger. Hence, the ratio of reduction of road friction coefficient $\mu$ to an increase of yaw rate deviation dispersion is established to be small.

Figure 3:
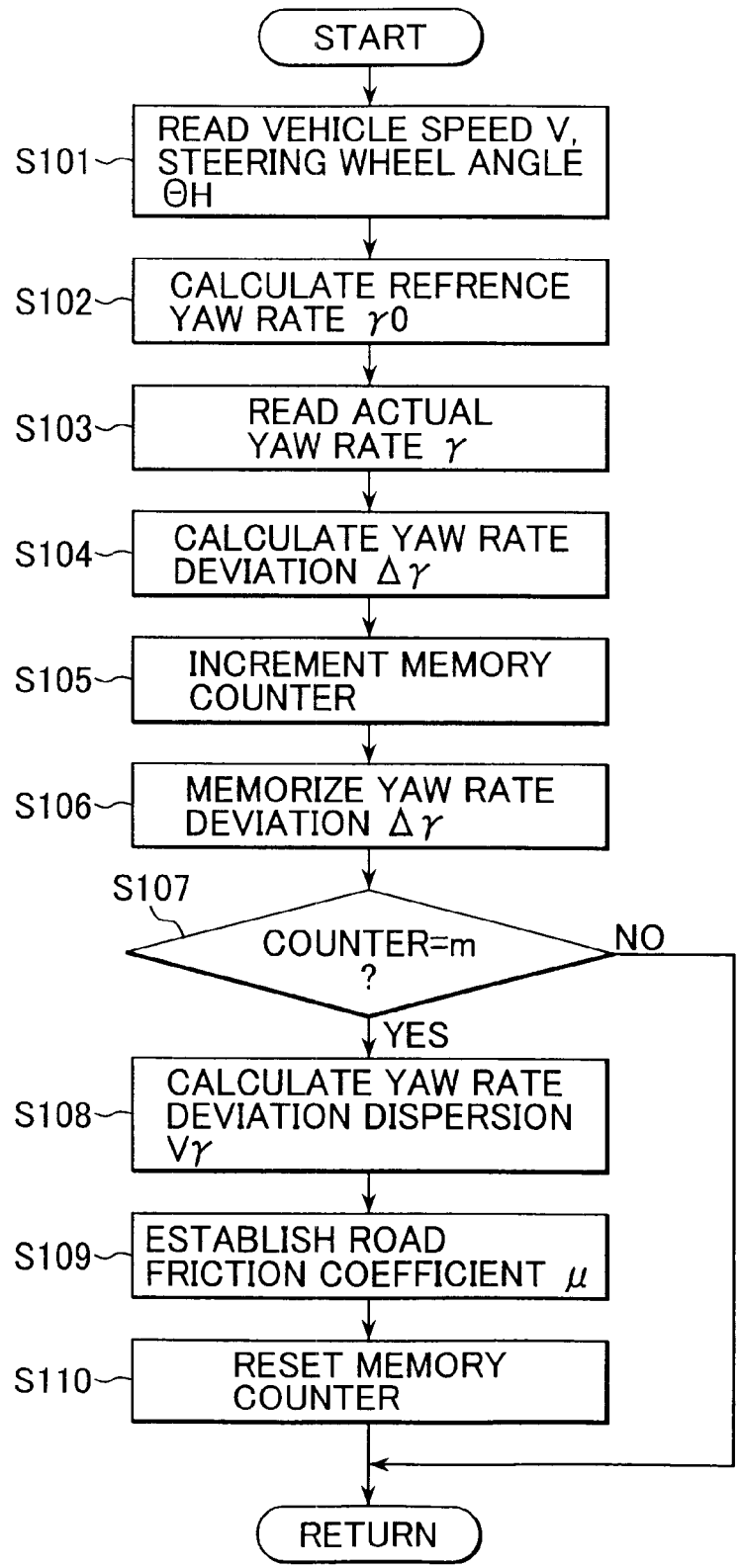
FIG. 3 is a flowchart showing steps of the estimation of road friction coefficients in the apparatus according to the first embodiment.

Next, an estimation process of road friction coefficient will be described by reference to a flowchart of FIG. 3. This program is executed at a specified time interval. At a step (hereinafter referred to as S) 101, a vehicle speed V and a steering wheel angle $\theta H$ are read from the vehicle speed sensor 2 and the steering wheel angle sensor 3, respectively. The program goes to S102 where a reference yaw rate $\gamma 0$ is calculated in the reference yaw rate calculating section 11 according to the aforesaid formula (1).

Then, the program goes to S103 where an actual yaw rate $\gamma$ is read from the yaw rate sensor 4 and goes to S104 where a yaw rate deviation $\Delta\gamma$ is calculated in the yaw rate deviation calculating section 12 according to the aforesaid formula (5).

Then, the program goes to S105 where a memory counter is incremented in the yaw rate deviation dispersion calculating section 13 and goes to S106 where the yaw rate deviation $\Delta\gamma$ outputted from the yaw rate deviation calculating section 12 is memorized.

At S107, it is checked whether or not the memory counter reaches a specified number of times (times of execution of the routine or times of execution of the routine within a specified time span) "m". If the counter does not reach the specified number of times m, the program leaves the routine and if the counter reaches the specified number of times m, the program goes to S108.

At S108, a yaw rate deviation dispersion $V\gamma$ at the sampling number m is calculated according to the aforesaid formula (6) and the program goes to S109.

At S109, a road friction coefficient is established in the road friction coefficient establishing section 14 by referring to a map showing a road friction coefficient $\mu$ versus a yaw rate deviation dispersion $V\gamma$.

Then, the program goes to S110 where the memory counter is reset and leaves the routine.

Thus, according to the first embodiment, since the road friction coefficient $\mu$ is estimated based on a yaw rate deviation dispersion $V\gamma$, that is, not an absolute value of yaw rate but a dispersion obtained by statistically processing the yaw rate deviation $\Delta\gamma$, the influence of sensor resolution, zero correction, noise and the like can be minimized. Further, an accurate road friction coefficient can be estimated without vibratory steering inputs. Further, since the relationship between road friction coefficient $\mu$ and yaw rate deviation dispersion $V\gamma$ is corrected according to vehicle speed V, more accurate road friction coefficient $\mu$ can be estimated.

Figure 4:
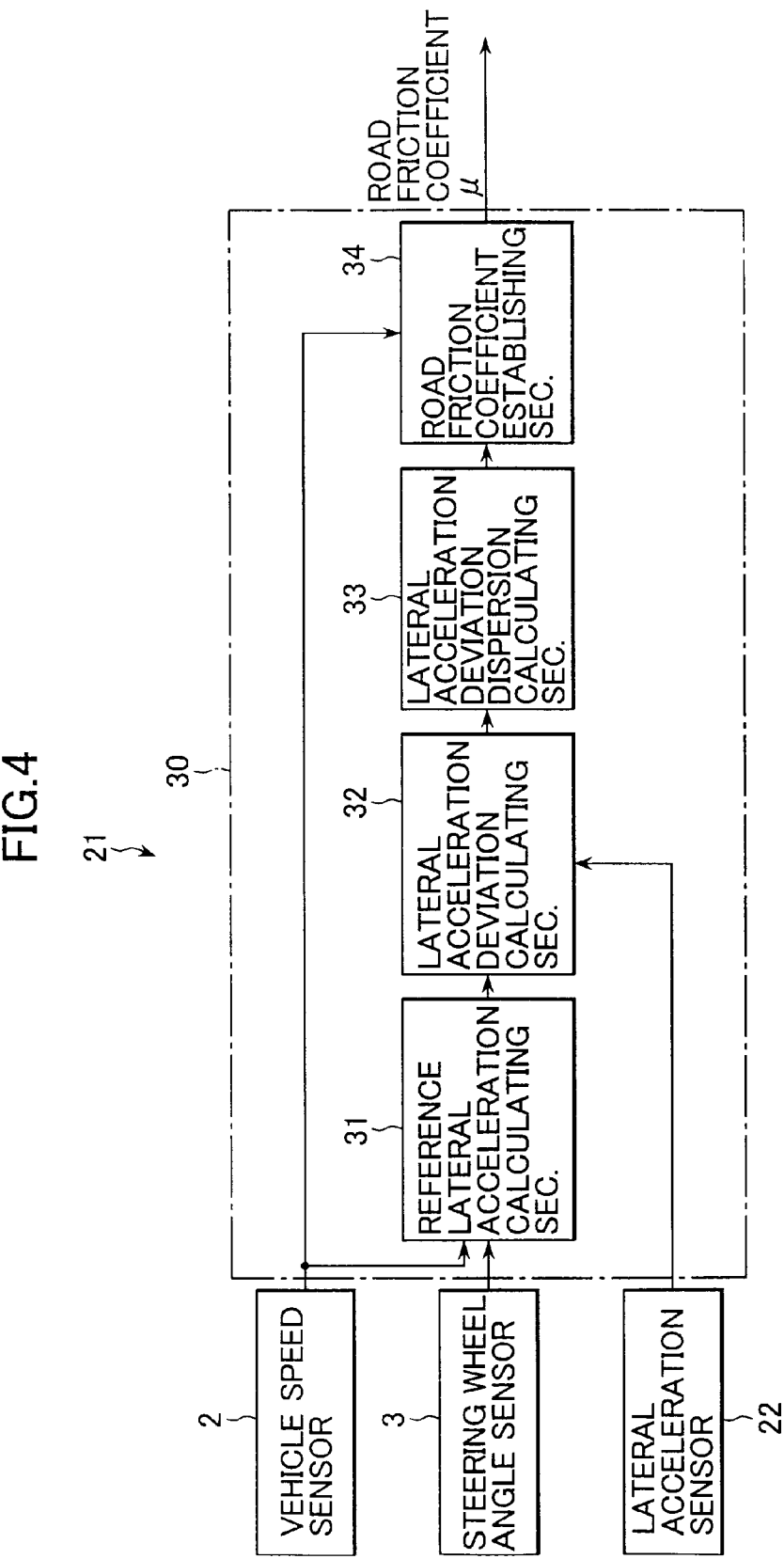
FIG. 4 is a functional block diagram showing a road friction coefficient estimating apparatus according to a second embodiment of the present invention.
Figure 5:
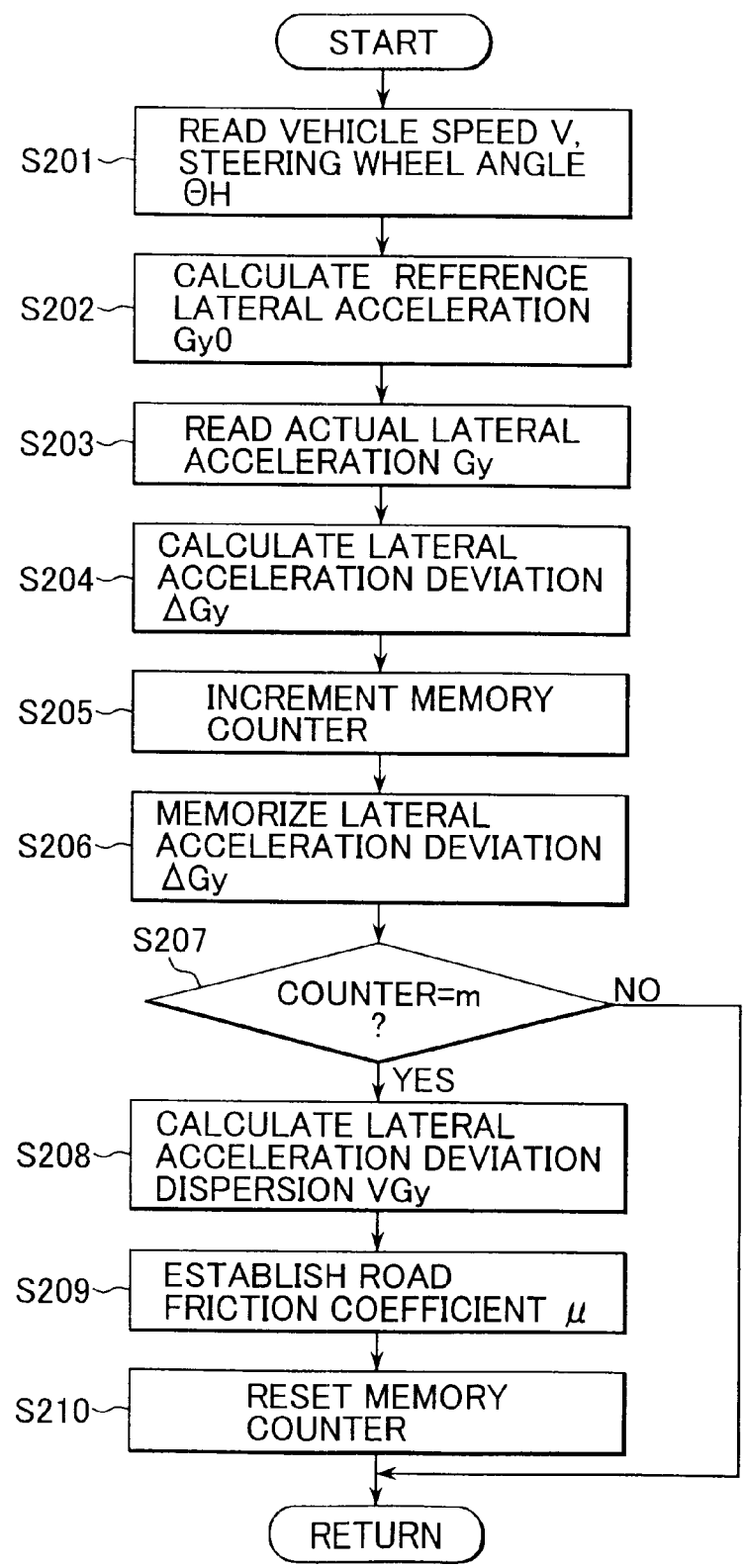
FIG. 5 is a flowchart showing steps of the estimation of road friction coefficients in the apparatus according to the second embodiment.

FIGS. 4 and 5 show a second embodiment of the present invention. In the second embodiment, lateral acceleration plays a role of parameter representing the condition of motion of a vehicle.

FIG. 4 is a functional block diagram showing a road friction coefficient estimating apparatus according to the second embodiment of the present invention. In the drawing, reference numeral 21 denotes a road friction coefficient estimating apparatus for estimating road friction coefficients, whose control section 30 is connected with a vehicle speed sensor 2, a steering wheel angle sensor 3 and a lateral acceleration sensor 22 and inputs a vehicle speed V indicative signal, a steering wheel angle $\theta H$ and a lateral acceleration Gy indicative signal, respectively.

The control section 30 of the road friction coefficient estimating apparatus 21 is constituted by a micro-computer and peripheral circuits and functionally constituted by a reference lateral acceleration calculating section 31, a lateral acceleration deviation calculating section 32, a lateral acceleration deviation dispersion calculating section 33 and a road friction coefficient establishing section 34.

The reference lateral acceleration calculating section 31 inputs a vehicle speed V indicative signal from the vehicle following formula (7) based on a vehicle motion model:

$$Gy0=(Gy\delta(\theta H/n))/(1+tr \cdot s) \quad (7)$$

where $Gy\delta$ is a lateral acceleration gain, which is expressed as follows:

$$Gy\delta=(1/(1+A \cdot V^2))(V^2/L) \quad (8)$$

Thus, according to the formula (7), the reference lateral acceleration Gy0 is obtained in consideration of dynamic lag. Accordingly, even when a driver makes a fast steering, an accurate value of the reference lateral acceleration Gy0 can be obtained.

The lateral acceleration deviation calculating section 32 inputs an actual lateral acceleration Gy from the lateral acceleration sensor 22 and inputs a reference lateral acceleration Gy0 from the reference lateral acceleration calculating section 31. The lateral acceleration deviation calculating section 32 calculates a deviation ΔGy (lateral acceleration deviation) of the actual lateral acceleration Gy from the reference lateral acceleration Gy0 and outputs the deviation to the lateral acceleration deviation dispersion calculating section 33.
That is:

$$\Delta Gy = Gy - Gy0 \quad (9)$$

The lateral acceleration deviation dispersion calculating section 33 inputs a lateral acceleration deviation ΔGy from the lateral acceleratin deviation calculating section 32 and calculates a dispersion VGy of the lateral acceleration deviation ΔGy in a predetermined sampling number according to the following formula (10). The calculated dispersion VGy is outputted to the road friction coefficient establishing section 34.

$$VGy = (1/m)\Sigma(\Delta Gyi - \Delta Gyc)^2 \quad (10)$$

where m is a total sampling number; i is a data number of the lateral acceleration deviation ΔGy; ΔGyc is an average of the total lateral acceleration deviations ΔGy for the sampling number m; and Σ is a sum from 1 to m.

The road friction coefficient establishing section 34 inputs a vehicle speed V from the vehicle speed sensor 2 and a lateral acceleration deviation dispersion VGy from the lateral acceleration deviation dispersion calculating section 33, respectively and establishes a road friction coefficient μ based on these values.

Specifically, the road friction coefficient μ is established by referring to a look-up table (not shown). The table is prepared experimentally beforehand based on the relationship per vehicle speed V between road friction coefficient μ and lateral acceleration deviation dispersion VGy. Further, in the same manner as in the first embodiment, as road friction coefficient μ becomes low, lateral acceleration deviation dispersion VGy becomes larger. Further, as vehicle speeds go up, the ratio of reduction of road friction coefficient μ to an increase of lateral acceleration deviation dispersion VGy is established to be smaller. as road friction coefficient μ becomes low, lateral acceleration deviation dispersion VGy becomes larger. Further, as vehicle speeds go up, the ratio of reduction of road friction coefficient μ to an increase of lateral acceleration deviation dispersion VGy is established to be smaller.

Next, an estimation process of road friction coefficient in the road friction coefficient estimating apparatus 21 will be described by reference to a flowchart of FIG. 5. This program is executed at a specified time interval. First, at S201, a vehicle speed V and a steering wheel angle θH are read from the vehicle speed sensor 2 and the steering wheel angle sensor 3, respectively. The program goes to S202 where a reference lateral acceleration Gy0 is calculated in the reference lateral acceleration calculating section 31 according to the aforesaid formula (7).

Then, the program goes to S203 where an actual lateral acceleration Gy is read from the lateral acceleration sensor 22 and goes to S204 where a lateral acceleration deviation ΔGy is calculated in the lateral acceleration deviation calculating section 32 according to the aforesaid formula (9).

Then, the program goes to S205 where a memory counter is incremented in the lateral acceleration deviation dispersion calculating section 33 and goes to S206 where the lateral acceleration deviation ΔGy outputted from the lateral acceleration deviation calculating section 32 is memorized.

At S207, it is checked whether or not the memory counter reaches a specified number of times (times of execution of the routine or times of execution of the routine within a specified time span) "m". If the counter does not reach the specified number of times m, the program leaves the routine and if the counter reaches the specified number of times m, the program goes to S208.

At S208, a lateral acceleration deviation dispersion VGy at the sampling number m is calculated and the program goes to S209.

At S209, a road friction coefficient is established in the road friction coefficient establishing section 34 by referring to a look-up table showing road friction coefficient μ versus yaw rate deviation dispersion VGy.

Then, the program goes to S210 where the memory counter is reset and leaves the routine.

Thus, according to the second embodiment of the present invention, since the road friction coefficient μ is estimated based on a lateral acceleration deviation dispersion VGy, that is, not an absolute value of lateral acceleration but a dispersion obtained by statistically processing the lateral acceleration deviation ΔGy, the influence of sensor resolution, zero correction, noise and the like can be minimized. Further, an accurate road friction coefficient can be estimated without vibratory steering inputs.

Figure 6:
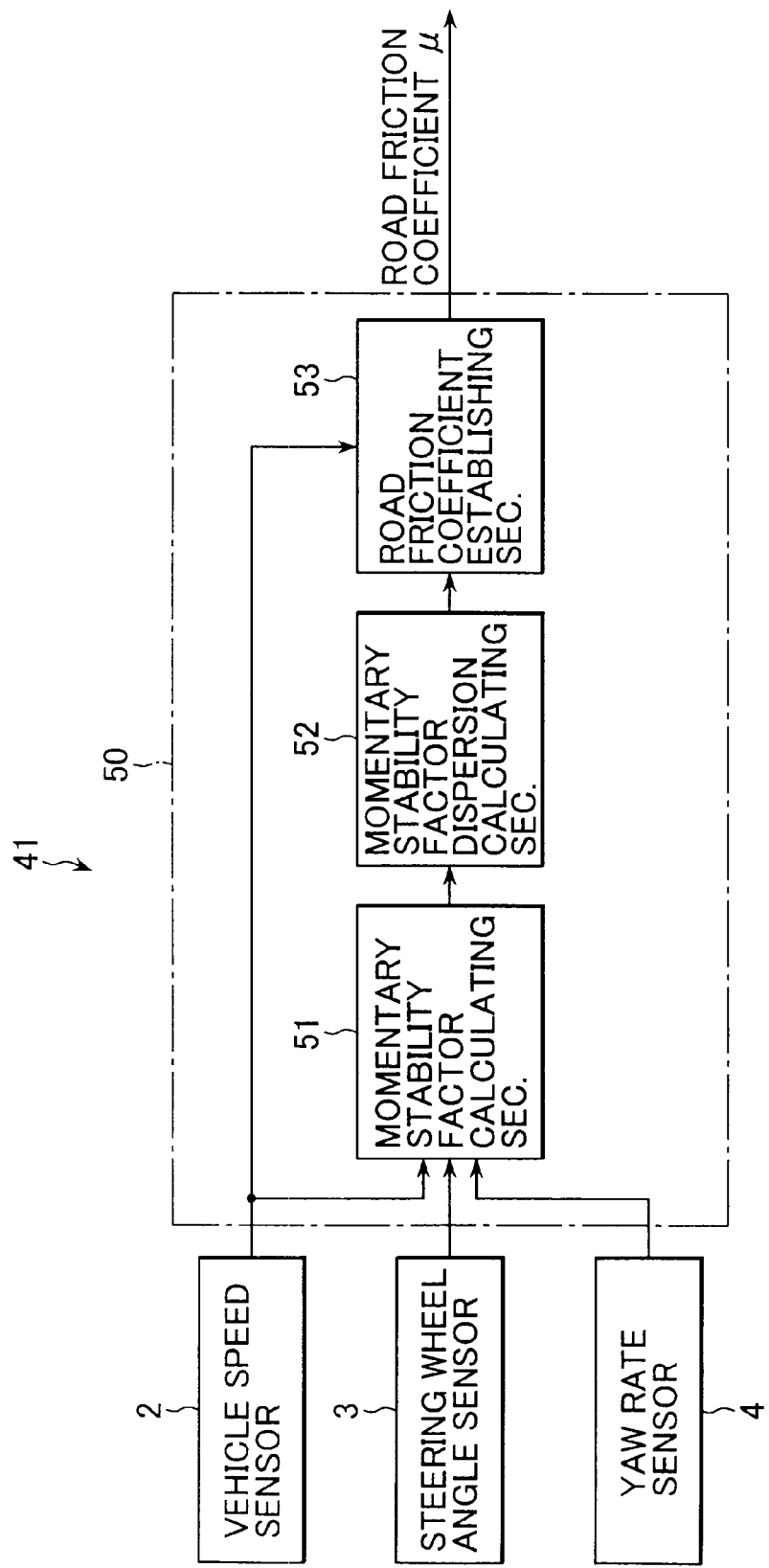
FIG. 6 is a functional block diagram showing a road friction coefficient estimating apparatus according to a third embodiment of the present invention.
Figure 7:
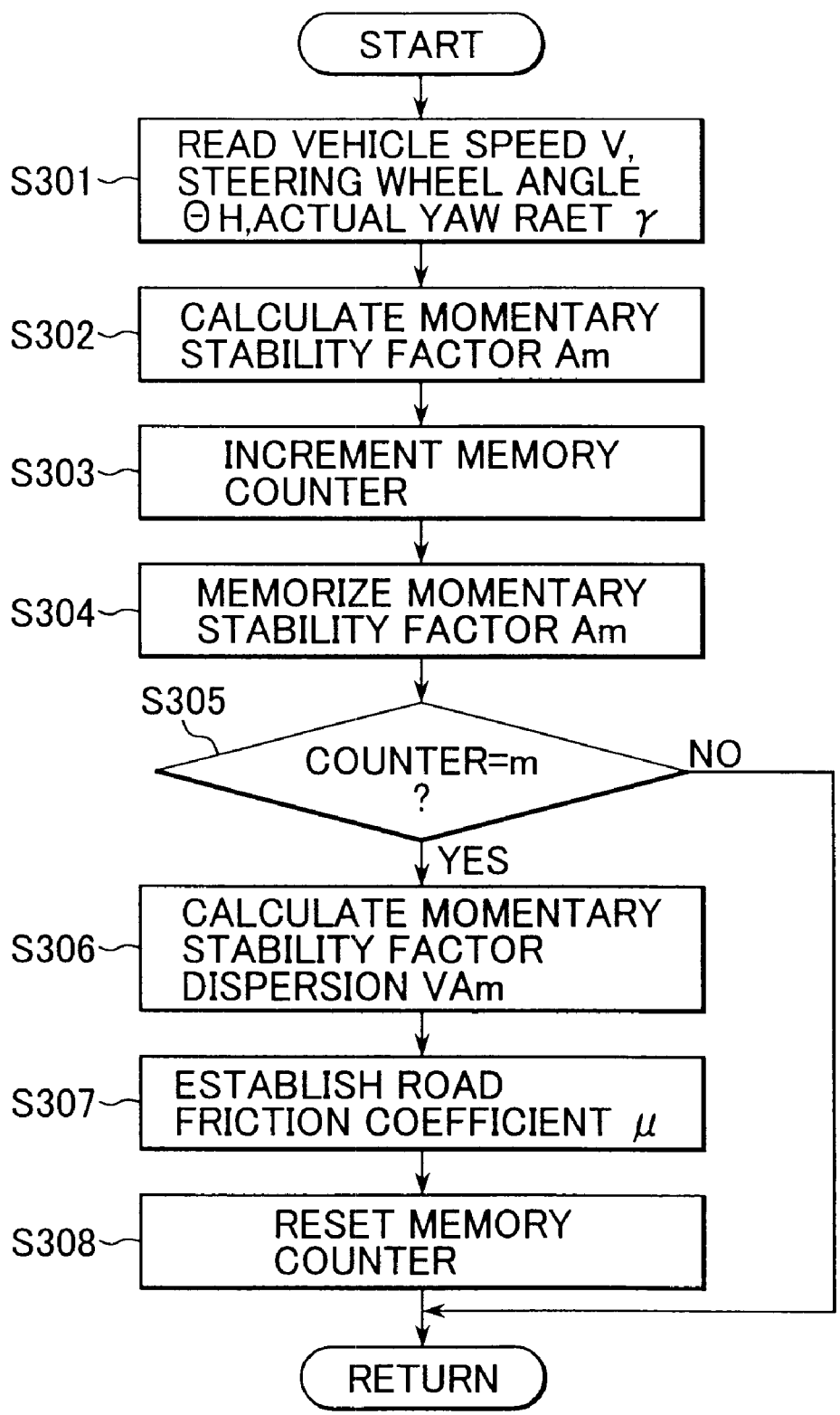
FIG. 7 is a flowchart showing steps of the estimation of road friction coefficients in the apparatus according to the third embodiment.

Next, FIGS. 6 and 7 show a third embodiment of the present invention. According to this embodiment, a steering characteristic (momentary stability factor) detected at each moment by a sensor play a role of a parameter for obtaining dispersion.

Referring to FIG. 6, reference numeral 41 denotes a road friction coefficient estimating apparatus for estimating road friction coefficients. A control section 50 of the road friction coefficient estimating apparatus is connected with the vehicle speed sensor 2, the steering wheel angle sensor 3 and the yaw rate sensor 4 for inputting a vehicle speed V indicative signal, a steering wheel angle θH indicative signal and a yaw rate γ indicative signal, respectively.

The control section 50 of the road friction coefficient estimating apparatus 41 is constituted by a micro-computer and peripheral circuits and functionally constituted by a momentary stability factor calculating section 51, a momentary stability factor dispersion calculating section 52 and a road friction coefficient establishing section 53.

The momentary stability factor calculating section 51 inputs a vehicle speed V indicative signal from the vehicle speed sensor 2, a steering wheel angle θH indicative signal from the steering wheel angle sensor 3 and a yaw rate γ indicative signal from the yaw rate sensor 4, respectively and calculates a momentary stability factor Am according to the following formula (11) based on a vehicle motion model:

$$Am = (((\theta H/n)/\gamma) \cdot (V/L) - 1)/V^2 \quad (11)$$

The momentary stability factor dispersion calculating section 52 inputs the momentary stability factor Am from the momentary stability factor calculating section 51 and calculates a dispersion VAm of the momentary stability factor Am at a predetermined sampling number according to the following formula (12):

$$VAm = (1/m)\Sigma(Ami - Amc)^2 \quad (12)$$

where m is a total sampling number; i is a data number of the momentary stability factor Am; Amc is an average of the total momentary stability factor Am for the sampling number m; and $\Sigma$ is a sum from 1 to m.

The road friction coefficient establishing section 53 inputs a vehicle speed V indicative signal from the vehicle speed sensor 2 a momentary stability factor dispersion VAm from the momentary stability factor dispersion calculating section 52 and establishes a road friction coefficient $\mu$ based on these.

Specifically, the road friction coefficients is established by referring to a table (not shown). The table is similar to the table shown in FIG. 2 and prepared experimentally beforehand based on the relationship per vehicle speed V between road friction coefficient $\mu$ and momentary stability factor dispersion VAm. Further, in the same manner as in the first embodiment, as road friction coefficient $\mu$ becomes lower, stability factor deviation dispersion VAm becomes large. Further, as vehicle speeds go up, the ratio of reduction of road friction coefficient $\mu$ to an increase of stability factor dispersion VAm is established to be small.

Next, a flow of the processing of road friction coefficient estimation in the road friction coefficient estimating apparatus 41 will be described by referring to a flowchart of FIG. 7. This program is carried out at a specified time interval. First, at S301, a vehicle speed V, a steering wheel angle θH and a yaw rate γ are read from the vehicle speed sensor 2, the steering wheel angle sensor 3 and the yaw rate sensor 4, respectively. The program goes to S302 where a momentary stability factor Am is calculated in the momentary stability factor calculating section 51 according to the aforesaid formula (11).

Then, the program goes to S303 where a memory counter is incremented in the momentary stability factor dispersion calculating section 52 and goes to S304 where the momentary stability factor Am outputted from the momentary stability factor calculating section 51 is memorized.

At S305, it is checked whether or not the memory counter reaches a specified number of times (times of execution of the routine or times of execution of times within a specified time span) "m". If the counter does not reach the specified number of times m, the program leaves the routine and if the counter reaches the specified number of times m, the program goes to S306.

At S306, a momentary stability factor dispersion VAm at the sampling number m is calculated in accordance with the formula (12) and the program goes to S307.

Further, at S307, a road friction coefficient is established in the road friction coefficient establishing section 53 by referring to a look-up table established per vehicle speed V and showing road friction coefficient $\mu$ versus momentary stability factor dispersion VAm.

Then, the program goes to S308 where the memory counter is reset and leaves the routine.

Thus, according to the third embodiment of the present invention, since the road friction coefficient $\mu$ is estimated based on a momentary stability factor dispersion VAm, that is, not a dispersion obtained by statistically processing a steering characteristic of a vehicle at each moment, the influence of sensor resolution, zero correction, noise and the like can be minimized. Further, an accurate road friction coefficient can be estimated without vibratory steering inputs.

While the presently preferred embodiments of the present invention have been shown and described, it is to be understood that these disclosures are for the purpose of illustration and that various changes and modifications may be made without departing from the scope of the invention as set forth in the appended claims.

What is claimed is:

1. A road friction coefficient estimating apparatus for a vehicle, comprising:
    a reference value calculating means for calculating a reference value of a parameter indicative of a condition of motion of said vehicle;
    an actual value detecting means for detecting an actual value of said parameter;
    a deviation calculating means for calculating a deviation of said actual value from said reference value;
    a dispersion calculating means for calculating a dispersion obtained by statistically processing said deviation with a specified sampling number; and
    a road friction coefficient establishing means for establishing a road friction coefficient based on said dispersion.

2. The apparatus according to claim 1, wherein said parameter is a yaw rate of said vehicle.

3. The apparatus according to claim 1, wherein said parameter is a lateral acceleration of said vehicle.

4. The apparatus according to claim 1, wherein said road friction coefficient establishing means includes a table means in which said road friction coefficient is established by referring to a look-up table.

5. The apparatus according to claim 4, wherein said look-up table includes such a relationship that said road friction coefficient becomes smaller as said dispersion becomes large and said road friction coefficient becomes larger as said dispersion becomes small.

6. The apparatus according to claim 5, wherein said look-up table also includes such a relationship that a rate of reduction of said road friction coefficient to an increase of said dispersion is established to be smaller as a vehicle speed goes up.

7. The apparatus according to claim 1, wherein said specified sampling number is a preestablished number of times of execution of a routine for estimating said road friction coefficient.

8. The apparatus according to claim 1, wherein said specified sampling number is a number of times of execution of a routine for estimating said road friction coefficient within a preestablished time span.

9. A road friction coefficient estimating apparatus for a vehicle, comprising:
    a momentary steering characteristic calculating means for calculating a steering characteristic at each moment of said vehicle based on an actual condition of motion of said vehicle;
    a dispersion calculating means for calculating a dispersion obtained by statistically processing said steering characteristic with a specified sampling number; and
    a road friction coefficient establishing means for establishing a road friction coefficient based on said dispersion.

10. The apparatus according to claim 9, wherein said road friction coefficient establishing means includes a table means in which said road friction coefficient is established by referring to a look-up table.

11. The apparatus according to claim 10, wherein said look-up table includes such a relationship that said road friction coefficient becomes smaller as said dispersion becomes large and said road friction coefficient becomes larger as said dispersion becomes small.

12. The apparatus according to claim 11, wherein said look-up table also includes such a relationship that a rate of reduction of said road friction coefficient to an increase of said dispersion is established to be smaller as a vehicle speed goes up.

13. The apparatus according to claim 9, wherein said specified sampling number is a preestablished number of times of execution of a routine for estimating said road friction coefficient.

14. The apparatus according to claim 9, wherein said specified sampling number is a number of times of execution of a routine for estimating said road friction coefficient within a preestablished time span.

* * * * *